United States Patent [19]
Etienne

[11] Patent Number: 4,811,727
[45] Date of Patent: Mar. 14, 1989

[54] RETENTION STOCKING FOR LOWER LIMB

[76] Inventor: Abel Etienne, 29, rue des Carrieres, 57050 Plappeville, France

[21] Appl. No.: 910,603

[22] Filed: Sep. 23, 1986

[30] Foreign Application Priority Data

Sep. 26, 1985 [FR] France ................. 85 14412

[51] Int. Cl.⁴ ............................................. A61L 3/00
[52] U.S. Cl. .............................. 128/80 R; 128/80 F; 128/80 G; 128/165; 2/241; 2/DIG. 1
[58] Field of Search ............ 2/240, 241, 242, DIG. 1; 128/80 R, 80 E, 80 F, 80 H, 165, 166, 171

[56] References Cited

U.S. PATENT DOCUMENTS

| | | | |
|---|---|---|---|
| 2,646,797 | 7/1953 | Scholl | 128/165 |
| 3,916,886 | 11/1975 | Rogers | 128/80 E |
| 4,166,460 | 9/1979 | Applegate | 128/80 H |
| 4,206,515 | 6/1980 | Robinson | 2/241 |
| 4,502,158 | 3/1985 | Mouri et al. | 2/240 |
| 4,502,301 | 3/1985 | Swallow et al. | 128/165 |
| 4,722,099 | 2/1988 | Kratz | 2/DIG. 1 |

FOREIGN PATENT DOCUMENTS

| | | | |
|---|---|---|---|
| 0108510 | 9/1939 | Australia | 128/165 |
| 0465762 | 1/1969 | Czechoslovakia | |
| 0632595 | 1/1928 | France | 128/165 |
| 1111157 | 10/1955 | France | |
| 1124140 | 6/1956 | France | |
| 2347922 | 11/1977 | France | |
| 0206271 | 11/1923 | United Kingdom | 128/165 |
| 0318668 | 9/1929 | United Kingdom | 128/165 |

Primary Examiner—Richard J. Apley
Assistant Examiner—Paul Prebilic
Attorney, Agent, or Firm—Sandler & Greenblum

[57] ABSTRACT

A therapeutic support stocking made from a fabric of non-constricting flexible elastic fibers which extends from an area completely covering the toes to an area above the bend in the knee at the back of the leg and is held in place by an elastic band. The stocking is lined with a smooth, absorbent, and washable material. A plurality of ventilation and traction eyelets are located in the fabric only at the lateral parts of its leg segment. Embedded within the stocking are a pair of pads designed to fill the retromalleolar cavities to cushion and protect the Achilles tendon. A plastic, chamfered heel piece is further provided to antevert the axis of the leg to relieve tension in the Achilles tendon. An ankle support is additionally included, connected to the remainder of the stocking through an elastic transition zone to prevent constriction of the foot. The stocking is designed to support, cushion, and relieve tension in a number of indissociable components of the leg and to stimulate vascular circulation.

17 Claims, 1 Drawing Sheet

RETENTION STOCKING FOR LOWER LIMB

BACKGROUND OF THE INVENTION

1. Field of the Invention

The invention relates to a support stocking, in particular to the retentive support of the anatomopathological axis formed by the plantar arch, the Achilles tendon, the ischiatic leg muscles, the adductors, the pubis, the dorso-lumbar hinge joint and the pelvis, and adapted to the concomitant functions of maintenance, support, relief, compensation, protection, reinforcement of the operation of the muscular, articular, vascular and tendinous systems.

2. Description of Background and Relevant Information

An athlopathic epidemic exists in the hinge joints and in the tendons and ligaments thereof, of the lower limbs of humans and, more particularly, of athletes. It is, more or less, permanently endemic to certain sporting activities, football particularly. More specifically, the problem involves sclero-fibrous inflammatory affections and extreme overexertion and whose foundation is the fiber of the cell of the major systems of the locomotor apparatus and, therefore, of the system permitting movement, i.e., the muscular, ligamentary and tendinous apparatus with which the vascular system is intimately associated.

This athlopathic epidemic results from certain causes. One of the first causes is related to the living environment, i.e., the conditions of training, the hygienodietetic "atmosphere" throughout the year and, specifically, in the immediate period following competition. Thus, the athlete typically has poor hygiene and a poor diet which, in the periods immediately following intense physical activity, fail to place him in the ideal conditions for recovery.

Another cause is found in the sporting environment itself, such as hard soil, including synthetic turf. Improper equipment and "therapeutic" devices are a further cause. Now available on the market are ankle supports, elastic and adhesive bandages which give constrictive support. These products are said to be protective but in reality, are aggressive and traumatizing in the long term. They include, for example, shoes without heels, or with very low heels, which do not take into account plantar statics or dynamics but, instead, only fashion.

Further causes are the so-called "minefields". These include repeated micro-traumatisms which seem impossible to eliminate, i.e., the hidden efflorescence of inflammation sources that are not precisely located. Another "minefield" consists in metabolic changes (uric acid is a particular dietetic example of this). This is attributable to athletes not eating correctly, thereby producing in their bodies deposits of toxic elements which are not eliminated. After intense exercise, when the cells need recuperation in an environment which is ideal with respect to oxygen content, athletes tend to celebrate their victories with alcoholic drinks, thus adding to the toxic elements, even though alcoholic drinks should be taken only when one is fully rested and has recuperated.

Another "minefield" consists of malformations which are either neglected or not diagnosed, or bad habits at all levels. Another cause is the sapping and the discharging work of a muscular group, a tendon, or necessarily, therefore; of a joint, in response to a benign or recent traumatism, but which is one controlled by the subconscious (loco-regional or distant contraction, control-lateral or overlying or underlying). Thus, when a foot, a thigh or any part of a limb is traumatized, compensation is had by the control-lateral limb. This compensation, which is subconscious, partly to spare the effort of the traumatized limb, induces the control-lateral limb to increase its work which causes a contracting phenomena in the latter. Hence, not only must the affected limb be taken into account, but also the limb which is taking over part of its work.

In conclusion, all these factors induce, encourage, maintain, and fix in a preferential orbit of chronicity, the anatomical impairment of the athlete in the medium and long term. The muscles, vessels, joints, tendons and ligaments, all components which differ in nature, are interdependent and physiologically and pathologically dependent. All these elements not only work separately, but also in relation to one another, both under normal conditions as well as under conditions of traumatisms and injuries. Thus, when a muscle is affected a tendon necessarily suffers; when a tendon suffers, then a joint suffers as well; and so on. This additionally creates potential circulation problems since additional oxygen is needed to be produced because of the injury to the muscle, the tendon, the joint, and to other components.

Without any particular order or preference, the plantar arch, the Achilles tendon, the ischiatic leg muscles, thus the muscles extending from the leg to the thigh, the adductors, the pubis, the dorso-lumbar hinge joint, and the pelvis form an entity, i.e., a whole, whose components are by their very nature, indissociable, especially on the therapeutic level. This is why, when a single component is injured and/or damaged in any way, the proposal to treat it by measures directed specifically at the affected component is mistaken. On the contrary, it is necessary to take the whole entity into account. In spite of this, evidence is provided every day that this elementary consideration is absent or is not heeded.

SUMMARY OF THE INVENTION

An object of this invention is to provide a retentive support which is specific in its action of stimulating venous circulation and of simultaneously increasing the dynamics of the plantar arch, specifically supporting the Achilles tendon and ensuring the proper return flow of the blood, while at the same time addressing a specific pathology. This support is constructed to address, by means of its particular, fundamental, and indissociable elements, the existance and maintenance of specific problems including, e.g., the shin-splint.

For this purpose, the invention relates to a retentive supporting stocking, in particular a retentive support of the anatomo-pathological axis formed by the planter arch, the Achilles tendon, the ischiatic leg muscles, the adductors, the pubis, the dorso-lumbar hinge joint and the pelvis, and is adapted to the concomitant functions of maintenance, support, relief, compensation, protection, reinforcement of the operation of the muscular, articular, vascular and tendinous systems of the lower limbs.

According to one aspect of the invention, the stocking extends from a zone of total coverage of the toes to the whole of the legs, and it combines a fabric composed of flexible and non-constrictive elastic fibers and a fabric lining of a smooth, absorbent and washable material.

According to another aspect of the invention, the stocking includes ventilation and traction eyelets on the upper and lower lateral parts of the leg segment to facilitate proper ventilization of perspiration where it more generally appears, as well as to enable the wearer to more easily grasp and pull the stocking onto the leg.

According to another aspect of the invention, the stocking also includes a subgonal elastic band located at an upper circumference, beneath the knee extending from the front juxtaratolian up to the rear of the lower part of the upper triangle of the popliteal hollow.

According to a still further aspect of the invention, the stocking includes, embedded in its thickness, two bean-shaped pads which substantially fill up the retromalleolar cavities situated on either side of the Achilles tendon, to thereby support and cushion the tendon.

According to a still further aspect of the invention, the stocking includes a chamfered heel-piece with a height of about five millimeters. The heel-piece is preferably made from a plastic material, such as polyethylene, and is a distinct element which is designated antevert the axis of the leg to relieve achillean tension.

According to a still further aspect of the invention, the stocking includes an ankle support and presents, at the level of the osteo-musculo-tendinous complex, an elastic area of transition extending from the middle part of the foot to the upper two thirds of the leg.

BRIEF DESCRIPTION OF THE DRAWINGS

The invention will be better understood by referring to the following description, given as a non-limiting example, and to the attached drawing in which.

DESCRIPTION OF PREFERRED EMBODIMENT

Figure 1:
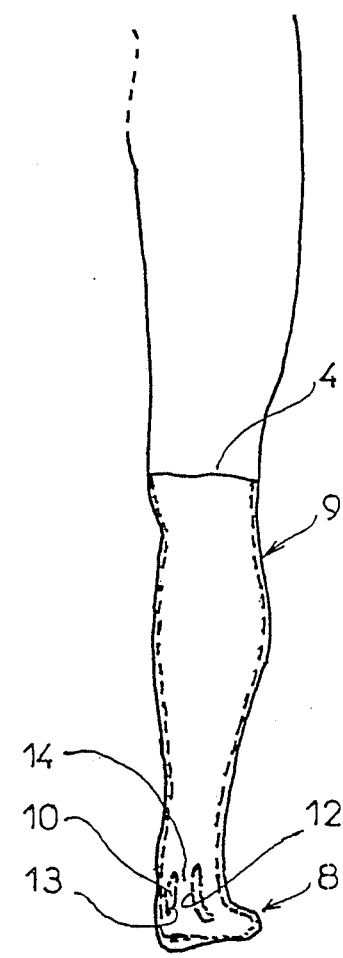
FIG. 1 is a view from behind of a lower limb fitted with the therapeutic support stocking according to the invention.
Figure 2:
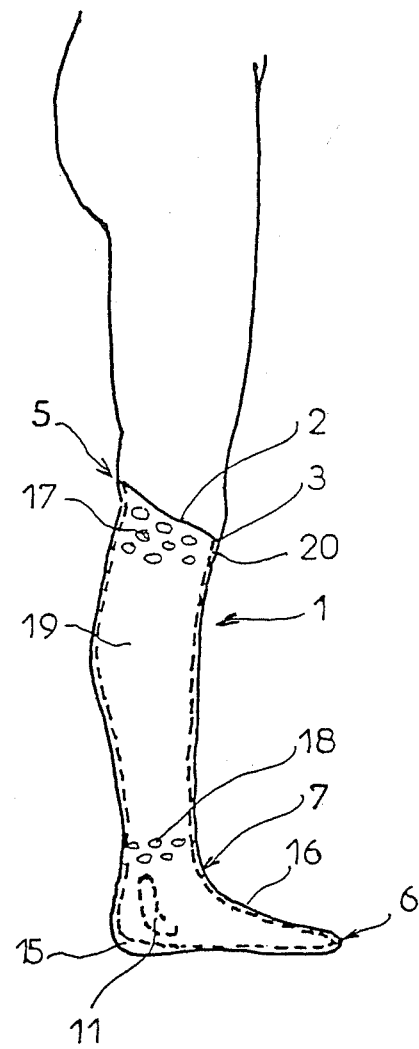
FIG. 2 is a lateral external view of this lower limb.

The stocking 1 is a prophylactic device, thus one for the prevention and therapy of a certain number of affections and injuries. A first affection and/or injury consists of a number of subjective problems associated with the leg-foot couple, without being precisely located, and in which the vascular, muscular, tendinous, osteoperiositic and articular discomforts are intimately linked and associated in a pathology which is quite obviously inflammatory and one of circulatory insufficiency. In this way, a state of overall suffering exists, triggered by a complex in which the causal element cannot be precisely determined.

A second affection and/or injury consists of (1) an inflammation which is either post-contusional or due to overexertion caused by training in poor conditions because of synthetic surfaces or seasonal hardness of the ground, in winter or in summer, or (2) an inflammation which is more precisely musculo-tendinous caused by excessive compensating forces by the muscles or other components of the control-lateral limb.

Another affection and/or injury consists of circulatory insufficiency or pain which may be located at the area of the neighboring venous, arterial, or capillary systems.

· According to the objects of the invention, the upper circumference 2 of the stocking 1 is at the front 3 juxtaratolian, whereas at the rear 4 it is located at the lower part 5 of the upper triangle of the popliteal hollow. In this way, any vascular compression is avoided at the bend in the leg, behind the knee. Further avoided by this configuration is the slipping of the stocking 1, in particular when it stops opposite the upper part of the hypertrophic calves.

The stocking 1 is composed of flexible elastic fibers which are non-constrictive and very degressive from the extremity of the toes. Said stocking 1 comprises a zone 6 which completely covers the toes. This eliminates any hypercompression at the base of the toes which would be caused by forces tending to retract support devices which are traditionally open at the toes. Thus, at the area of the base of the toes, these prior art devices produce a retraction exerted at the front of the foot. This causes the wearer of the support discomfort and very often obliges him to remove his shoe and readjust the front part of the stocking to remove this constriction.

The stocking 1 comprises a reinforcement 7 in the form of an ankle support at the area of the osteo-muscolotendinous complex of the ankle, but includes an elastic transition area to avoid any blood circulation problems, an inevitable source of discomfort, formications, heaviness, cramps, i.e., all subjective manifestations generating unexplained problems. In fact, if the support did not have this elastic transition area, there would be a risk of circulatory problems because of the zones of constriction at certain places on the leg, thus giving rise to overall discomfort.

This elastic transition area extends from the middle part 8 of the foot, and passes via the junction of the lower third to the upper two-thirds 9 of the leg.

The stocking of this invention also addresses problems at the area of the Achilles tendon including, in particular, the principal part of the tendon, as well as its whole anatomical course and its areas of attachment. These problems include bursitis, which is difficult to detect and which corresponds to the inflammation of a serous bursa situated between the Achilles tendon and the top part of the posterior face of the calcaneum; the simple lesion by contusion; partial breaks or cracks that are more or less recent; and the results of complete rupture, originally treated surgically.

For this purpose, the stocking 1 has means of support embedded in its thickness. These means of support are two pads 10, 11 which are bean-shaped and which fill up the retro-malleolar cavity 12, 13 on either side of the body 14 of the Achilles tendon. These pads 10, 11 ensure the support and the relief of vibrations or lateral movements caused either by the hardness of the ground or by excessive muscular dynamics due to over-training, overexertion and other reasons. These pads 10, 11 fit closely into the anatomy of the two depressions, thus blocking any friction of the stocking 1 on the posterior face of the tendon.

Another means of support according to the stocking of this invention consists of a chamfered heel-piece 15 of, e.g., polyethylene, having a height, for example, of five millimeters. The purpose of the heel-piece is to relieve achillean tension by providing a distinct element and by anteverting the axis of the leg. In this way, tension is reduced to avoid a hyperextension which could cause pain in the muscles of the calf and/or the thigh.

In addition, the stocking 1 serves as prophylactic and therapeutic equipment for:

muscular contractures, contusions, strains, elongations and tears;

simple or ossifying myosites;

hematoma, benign or serious, circumscribed or diffuse, necessarily calcified or encysted;

epiphysites and periostites, in particular pretibial;
sprains, benign or serious, plastered, or otherwise;
stiffnesses and ankyloses, post-traumatic or from immobilization;
circulatory insufficiencies of lympho-capillarovenous support.

For these reasons, the stocking 1 also includes a relaxation and a reduction in the thickness of the constrictive fibers at the level 16 of the foot, thus eliminating any irritation of the anteroir tendons.

The fabric of the stocking 1 is lined with a smooth, absorbent, washable material which makes it easy to slip on and reduces hyperhydrosis which is either independent of or is caused by such supports in general.

In addition, the stocking 1 includes ventilation and traction eyelets 17, 18 on the top and bottom lateral parts of the leg segments 19.

To avoid circulation problems, it is desirable to accommodate, without constriction, the variations of the anatomical profiles of the calf. For this purpose, the stocking 1 includes a subgonal elastic band 20.

For all the reasons cited above, the stocking according to the invention is an indispensible therapeutic device for all apparent and evident lesions and/or anomalies affecting the locomotor axis.

Although the invention has been described with reference to particular means, materials and embodiments, it is to be understood that the invention is not limited to the particulars disclosed and extends to all equivalents within the scope of the claims.

I claim:

1. A therapeutic retentive stocking for support of the anatomo-pathological axis of the leg, said axis defined by the plantar arch, the Achilles tendon, the ischiatic leg muscles, the adductors, the pubis, the dorso-lumbar hinge joint, and the pelvis, and for the concomitant functions of maintenance, support, relief, compensation, protection, and reinforcement of the operation of the muscular, articular, vascular, and tendinous systems, comprising:
   (a) a leg segment having an upper portion and a lower portion;
   (b) a foot segment;
   (c) a fabric of flexible, elastic, non-constricting fibers, said fabric having an inner surface;
   (d) a closed end and an open end, said closed end adapted to completely enclose the toes, and said open end defining an upper circumference adapted to surround the leg from the juxtaratolian front to the lower part of the upper triangle of the popliteal hollow;
   (e) a lining attached to said inner surface of said fabric, said lining comprising a fabric of smooth, absorbent, washable material;
   (f) a plurality of ventilation and traction eyelets located in each of said upper portion and said lower portion adapted to be positioned against a lateral portion of the leg;
   (g) an elastic band located proximate said upper circumference and adapted to be located beneath the knee of said leg;
   (h) two bean-shaped pads embedded within the thickness of said stocking, each pad to be located adjacent the Achilles tendon and each pad having a thickness to fill the retro-malleolar cavity on either side of the Achilles tendon to thereby support the Achilles tendon;
   (i) a chamfered heel piece to be located at the heel, said heel piece being comprised of a plastic material, distinct from but attached to said fabric to antevert the axis of the leg and to relieve tension on the Achilles tendon;
   (j) an ankle support to be located at the osteo-musculotendinous complex of the ankle; and
   (k) an elastic transition zone position between said ankle support and said fabric, extending from a position adjacent the middle portion of the foot to the upper two-thirds of the lower leg to prevent constricting the leg adjacent said ankle support.

2. The stocking according to claim 1, wherein said fibers are adapted to apply forces which degrees from the extremity of the foot segment to the leg segment.

3. The stocking according to claim 1, wherein said heel piece has a height of approximately five millimeters.

4. The stocking according to claim 1 wherein said heel piece is made of polyethylene.

5. A stocking comprising:
   (a) a leg segment, having two lateral parts and, further, having an upper portion and a lower portion;
   (b) a foot segment connected to said lower portion of said leg segment, said foot segment having two lateral parts;
   (c) a plurality of ventilation and traction eyelets;
   (d) an elastic band located proximate said upper portion and adapted to be located beneath the knee of the leg;
   (e) at least one pad located at a lateral part of said foot segment;
   (f) a heel piece located at said foot segment to be substantially positioned beneath the heel when said stocking is worn; and
   (g) an ankle support located at said foot segment at the level of the osteo-muscolo-tendinous complex of the ankle when said stocking is worn;
   wherein said stocking comprises a fabric comprising flexible, elastic, non-constricting fibers, wherein said stocking has a closed end adjacent the toes, when said leg stocking is worn, wherein said upper portion of said segment comprises an open end, and wherein said stocking is adapted to completely enclose the leg from said closed end to said open end, except for said plurality of ventilization and traction eyelets, and wherein said stocking comprises an inner surface and a lining attached to said inner surface.

6. The stocking according to claim 5, wherein said pad is bean-shaped.

7. The stocking according to claim 5, wherein said pad has a thickness, shape, and is positioned to substantially fill one of the retro-malleolar cavities to cushion and support the Achilles tendon when said stocking is worn.

8. The stocking according to claim 7, wherein said at least one pad comprises two such pads, located at respective lateral parts of said foot segment.

9. A stocking according to claim 5, wherein said ventilation and traction eyelets are located only at said lateral parts of said leg segment in both said upper portion and said lower portion for ventilating the perspiration from the leg and, additionally, for enabling one to more easily grip and pull said stocking onto the leg.

10. A stocking according to claim 5, wherein said upper portion of said leg segment comprises an open end defining an upper circumference, adapted to surround the leg, when said stocking is worn, from the juxtaratolian front to the lower part of the upper triangle of the popliteal hollow to thereby avoid compression at the area where the upper leg bends relative to the lower leg.

11. A stocking according to claim 10, wherein said subgonal elastic band is located proximate said upper circumference to prevent said stocking from slipping.

12. A stocking according to claim 5, wherein said heel piece is comprised of a distinct plastic part.

13. A stocking according to claim 12, wherein said heel piece is chamfered and has a maximum thickness of approximately five millimeters.

14. The stocking according to claim 5, wherein said lining comprises a fabric of smooth, absorbent, washable material.

15. A stocking comprising:
    (a) a leg segment, having two lateral parts and, further, having an upper portion and a lower portion;
    (b) a foot segment connected to said lower portion of said leg segment, said foot segment having two lateral parts;
    (c) a plurality of ventilation and traction eyelets;
    (d) an elastic band located proximate said upper portion and adapted to be located beneath the knee of the leg;
    (e) at least one pad located at a lateral part of said foot segment;
    (f) a heel piece located at said foot segment to be substantially positioned beneath the heel when said stocking is worn; and
    (g) an ankle support located at said foot segment at the level of the osteo-muscolo-tendinous complex of the ankle when said stocking is worn;
    wherein said stocking comprises a fabric comprising flexible, elastic, non-constricting fibers, and wherein said ankle support is affixed to said stocking through an elastic transition zone between said ankle support and said fabric.

16. A stocking according to claim 15, wherein said elastic transition zone extends from a position adjacent the middle portion of said foot segment to a position adjacent the upper two-thirds of said leg segment.

17. A stocking comprising a fabric of flexible elastic, non-constricting fibers, said stocking further comprising:
    (a) a leg segment, having two lateral parts and, further, having an upper portion and a lower portion;
    (b) a foot segment connected to said lower portion of said leg segment, said foot segment having two lateral parts;
    (c) a plurality of ventilation and traction eyelets, wherein said ventilation and traction eyelets are located in said fabric and only at said lateral parts of said leg segment in both said upper portion and said lower portion for ventilating the perspiration from the leg and, additionally, for enabling one to more easily grip and pull said stocking onto the leg;
    (d) an elastic band located proximate said upper portion and adapted to be located beneath the knee of the leg;
    (e) at least one pad located at a lateral part of said foot segment;
    (f) a heel piece located at said segment to be substantially positioned beneath the heel when said stocking is worn; and
    (g) an ankle support located at said foot segment at the level of the osteo-muscolo-tendinous complex of the ankle when said stocking is worn.

* * * * *